United States Patent [19]

Grollier et al.

[11] Patent Number: 4,690,685
[45] Date of Patent: Sep. 1, 1987

[54] DYEING COMPOSITION FOR KERATINOUS FIBRES CONTAINING AT LEAST ONE CO-SOLUBILIZED N-SUBSTITUTED 2-NITRO-PARA-PHENYLENEDIAMINE

[75] Inventors: Jean-François Grollier, Paris; Jean Cotteret, Franconville; Alex Junino, Aulnay; Alain Genet, Neuilly Plaisance, all of France

[73] Assignee: L'Oreal, Paris, France

[21] Appl. No.: 780,606

[22] Filed: Sep. 26, 1985

[30] Foreign Application Priority Data

Sep. 27, 1984 [LU] Luxembourg .............. 85557

[51] Int. Cl.$^4$ .............. A61K 7/13
[52] U.S. Cl. .............. 8/405; 8/407; 8/408; 8/410; 8/415; 8/428; 8/435
[58] Field of Search .............. 8/405, 407, 408, 410, 8/415, 428, 435

[56] References Cited

U.S. PATENT DOCUMENTS 3,168,442  2/1965  Brunner et al. .............. 8/415
4,601,726  3/1987  Grollier et al. .............. 8/415

FOREIGN PATENT DOCUMENTS 2112818  7/1983  United Kingdom .............. 8/410
2150148  6/1985  United Kingdom .............. 8/415

Primary Examiner—Albert T. Meyers
Assistant Examiner—John M. Kilcoyne
Attorney, Agent, or Firm—Cushman, Darby & Cushman

[57] ABSTRACT

The invention relates to a dyeing composition for keratinous fibres containing at least one 4-bis($\beta$-hydroxyethyl)amino-2-nitro-1-(N-substituted amino)benzene compound in which the substitution is $C_1$–$C_3$ alkyl or $\beta$-hydroxyethyl; this composition contains as cosolubilization agent at least one dye of formula (II)

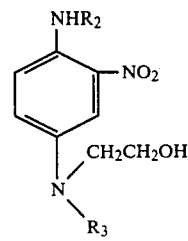

in which formula:
$R_2$ denotes a $C_2$–$C_3$ hydroxyalkyl group;
$R_3$ denotes a $C_2$–$C_3$ hydroxyalkyl group; with the proviso that, if $R_3=CH_2CH_2OH$, $R_2$ is necessarily an $\alpha$-hydroxyethyl or hydroxypropyl radical.

16 Claims, No Drawings

DYEING COMPOSITION FOR KERATINOUS FIBRES CONTAINING AT LEAST ONE CO-SOLUBILIZED N-SUBSTITUTED 2-NITRO-PARA-PHENYLENEDIAMINE

The present invention relates to a dyeing composition for keratinous fibres, and especially for living human hair, containing at least one nitrated direct dye of the N-substituted 2-nitro-para-phenylenediamine series. The invention also relates to a dyeing process using the said compositions.

It is known to use nitro-para-phenylenediamines are their substituted derivatives in dyeing solutions for dyeing keratinous fibres. These dyes endow the hair with a direct coloration also known as semi-permanent, and they can also be used in oxidation dyeing compositions to obtain, with the oxidation dyes, additional glints and shades rich in glints.

In hair dyeing, blue tints are necessary as components for achieving tints of natural appearance, and the use has already been proposed, as direct blue hair dyes, of 2-nitro-para-phenylenediamine derivatives in which the amino group in position 4 is disubstituted, the amino group in position 1 being, for its part, monosubstituted.

These classical 2-nitro-para-phenylenediamine derivatives are, more often than not, insufficiently soluble or dispersible in water, and this constitutes a major disadvantage in hair dyeing for achieving dark shades. In effect, if the dye is not solubilized in the dyeing medium, irregularities in dyeing are observed, with the great risk of obtaining weaker coloring than that envisaged; in the particular case of dyeing formulations rich in dyes for obtaining varied shades, or in the case of poorly solubilizing media, recrystallization of the dyes takes place and these remain in the dye bath and do not pass onto the hair.

Dyeing preparations produced from 2-nitro-paraphylenediamine derivatives in which the amino group in position 4 is disubstituted and in which the amino group in position 1 is monosubstituted have consequently not hitherto completely satisfied the demands of good dyeing.

Most surprisingly, we have discovered that, by introducing at least one N-($C_2$-$C_3$-hydroxyalkyl) derivative of 1-amino-2-nitro-4-[N'-($\beta$-hydroxyethyl)-N'-($C_2$-$C_3\omega$-hydroxyalkyl)]aminobenzene and/or at least one of its salts with an acid into a dyeing composition containing at least one blue nitrated direct dye consisting of a 2-nitro-para-phenylenediamine in which the amino group in position 4 is disubstituted with $\beta$-hydroxyethyl radicals and in which the amino group in position 1 is monosubstituted with a $C_1$-$C_3$ alkyl radical or a $\beta$-hydroxyethyl radical, the solubility of the blue nitrated direct dye or dyes was improved by a co-solubilization phenomenon.

The dyeing compositions according to the invention have the advantage of coloring the hair in intense, very deep shades, and in addition of enabling better use to be made of the potential dyeing power of the nitrated direct dye of the 2-nitro-para-phenylenediamine series, substituted as mentioned above.

In fact, on the one hand the N-($C_2$-$C_3$ hydroxyalkyl) derivatives of 1-amino-2-nitro-4-[N'-($\beta$-hydroxyethyl)-N'-($C_2$-$C_3\omega$-hydroxyalkyl)]aminobenzene are themselves blue dyes, strictly of the same shade as the nitrated direct dye to be co-solubilized, equivalent to a $\Delta H \leq 2.5$ according to the MUNSELL evaluation [for the MUNSELL notation, refer to the publication Official Digest, April 1964, pages 373 to 377, in which a color is defined by the formula HV/C, the parameters H, V and C designating, respectively, H the shade (or Hue), V the intensity (or Value) and C the purity or Chromaticity, the oblique stroke simply being a convention], so that it is possible to obtain darker shades than with the poorly soluble 2-nitro-para-phenylenediamine derivatives alone; and on the other hand the co-solubilizing agent introduced also makes it possible to avoid the risks of recrystallization of the nitrated direct dyes of the 2-nitro-para-phenylenediamine series in dyeing formulations having a poorly solubilizing medium.

The present invention accordingly provides a dyeing composition for keratinous fibres, and more especially for human hair, containing, in a suitable vehicle, at least one nitrated direct dye of the 2-nitro-paraphenylenediamine sries, of formula (I)

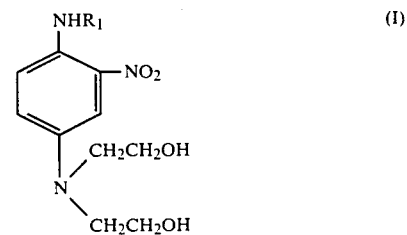

in which formula:

$R_1$ denotes a $C_1$-$C_3$ alkyl group or a $\beta$-hydroxyethyl group, the compound of formula (I) being able to take the form of the free base or a form salified with an inorganic or organic acid, characterized in that it also contains at least one compound of formula (II)

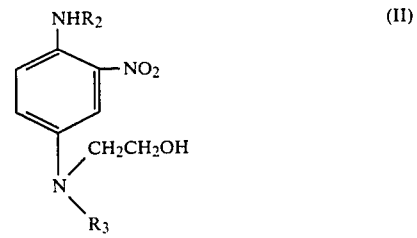

in which formula:

$R_2$ denotes a $C_2$-$C_3$ hydroxyalkyl group;

$R_3$ denotes a $C_2$-$C_3$ $\omega$-hydroxyalkyl group; with the proviso that, if $R_3$=$CH_2CH_2OH$, $R_2$ does not denote $\beta$-hydroxyethyl;

the compound of formula (II) being able to take the form of the free base or a form salified with an inorganic or organic acid.

Among the compounds of formula (I), the following are preferably used:

(a) compound of formula (I) in which $R_1$=methyl;

(b) compound of formula (I) for which $R_1$=$\beta$-hydroxyethyl.

These compounds have been described, in particular, in French Pat. Nos. 1,101,904, 1,411,124, and in U.S. Pat. No. 3,168,442.

Among the compounds of formula (II) which are especially usable as co-solubilization agents according to the invention, the following are preferably used:

(a) compound of formula (II) for which: $R_2=CH_2CH_2OH$ and $R_3=CH_2CH_2CH_2OH$, in the form of hydrochloride;

(b) compound of formula (II) for which: $R_2=CH_2CH_2CH_2OH$ and $R_3=CH_2CH_2OH$, in the form of hydrochloride;

(c) compound of formula (II) for which: $R_2=CH_2CHOHCH_3$ and $R_3=CH_2CH_2OH$, in the form of hydrochloride.

The compounds of formula (II) mentioned under (a) and (b) above are included in the general formula given in French Pat. No. 1,101,904, and the methods of preparation thereof are provided below in Examples A and B. The compound of formula (II) mentioned under (c) above can be prepared as described in Example C given below.

By way of explanation, the solubility limits at 18° C. of two dyes of formula (1) in the presence of increasing amounts y of a dye of formula (II) have been collated in the table which follows, these solubility limits being measured in the following composition:

| | |
|---|---|
| - monohydrochloride of dye of formula (II) | y g |
| - dye of formula (I) | x g |
| - ethylene glycol monoethyl ether | 10 g |
| - 2-amino-2-methyl-1-propanol q.s. | pH 9.6 |
| - water q.s. | 100 g | x is the maximum amount of the dye in question of formula (I) which can be dissolved in the particular medium thus defined. To determine the solubilities, the procedure is as follows:

A large excess of dye of formula (I) is dispersed with y g of product of formula (II), in the form of hydrochloride, in the cosmetic base described above. The composition is left for 15 minutes at 60° C. (waterbath) and then cooled by the ambient air with stirring for 30 minutes (checking that the ambient temperature is greater than 18° C.). After these 30 minutes, the composition is introduced into a chamber maintained at 18° C. The composition must remain there for at least 48 hours. After its removal from the chamber, the composition is immediately filtered. The collected filtrates are then analyzed by high performance liquid chromatography (HPLC) to determine the dye content.

| | | Solubility limits of the dye of formula (I) | | |
|---|---|---|---|---|
| | | Combined with the dye of formula (II) y = 1.5 g | | |
| Dye of formula (I) | alone y = 0 | NH—CH$_2$CH$_2$CH$_2$OH, NO$_2$, .HCl, N(CH$_2$CH$_2$OH)(CH$_2$CH$_2$OH) | NH—CH$_2$CH$_2$OH, NO$_2$, .HCl, N(CH$_2$CH$_2$OH)(CH$_2$CH$_2$CH$_2$OH) | NH—CH$_2$CHOHCH$_3$, NO$_2$, .HCl, N(CH$_2$CH$_2$OH)(CH$_2$CH$_2$OH) |
| NH—CH$_2$CH$_2$OH, NO$_2$, N(CH$_2$CH$_2$OH)(CH$_2$CH$_2$OH) | 0.74% | 2.13% (2.88)* | 1.31% (1.77)* | 1.90% (2.57)* |
| NH—CH$_3$, NO$_2$, N(CH$_2$CH$_2$OH)(CH$_2$CH$_2$OH) | 0.32% | 0.66% (2.06)* | | |

*The figure given in brackets shows the improvement in the solubility of the dye of formula (I) in the presence of the compound of formula (II). Thus, the dye of formula (I) indicated in the first line is 2.88 times more soluble in the aforementioned medium when the amount of the compound of formula (II) indicated in the 1st column in the said medium is present in an amount of 1.5 g.

According to preferred embodiments, the compound or compounds of formula (I) (and/or the salts) is/are present in the dyeing composition according to the present invention at a concentration of 0.05% to 10% by weight, and especially 0.1 to 5% by weight, expressed as free base, relative to the total weight of the composition; the compound or compounds of formula (II) (and/or the salts) is/are present in the composition at a concentration of 0.1 to 10% by weight, preferably 0.3 to 5% by weight, expressed as free base, relative to the total weight of the composition.

The dyeing compositions according to the invention can contain, in addition to the compounds of formulae (I) and (II), in free or salified form, for example:

(1) oxidation bases such as para-phenylenediamines, para-aminophenols and heterocyclic bases;

(2) one or more couplers belonging to the class of meta-phenylenediamines, meta-aminophenols or meta-diphenols, or to heterocyclic couplers, when the composition contains at least one oxidation base;

(3) ortho-phenylenediamines and ortho-aminophenols, optionally containing substituents on the ring or on the amino groups, or alternatively ortho-diphenol;

(4) dye precursors of the benzene series, containing on the ring at least three substituents chosen from the group consisting of hydroxy, methoxy or amino groups;

(5) dye precursors of the naphthalene series;

(6) leuco derivatives of indoanilines, indophenols or indoamines;

(7) nitrated direct dyes other than those of formulae (I) and (II);

(8) non-nitrated direct dyes such as azo dyes or anthraquinone dyes.

The dyeing compositions according to the invention can contain, as a suitable vehicle, water and/or organic solvents which are acceptable from the cosmetic standpoint and, more especially, alcohols such as ethyl alcohol, isopropyl alcohol, benzyl alcohol and phenylethyl alcohol, or glycols or glycol ethers such as ethylene glycol and its monomethyl, monoethyl and monobutyl ethers, propylene glycol, butylene glycol and dipropylene glycol, as well as alkyl ethers of diethylene glycol, such as diethylene glycol monoethyl ether and monobutyl ether, at concentrations of 0.5 to 20%, and preferably 2 to 10%, by weight relative to the total weight of the composition.

There can also be added to the composition according to the invention fatty amides, such as the mono- and diethanolamides of acids derived from copra, lauric acid or oleic acid, suitably at concentrations of 0.05 to 10% by weight.

Anionic, cationic, non-ionic or amphoteric surfactants, and mixtures thereof, can also be added to the composition according to the invention. The surfactants are preferably present in the composition according to the invention in a proportion from 0.1 to 50% by weight, and advantageously from 1 to 20% by weight, relative to the total weight of the composition.

Among surfactants, there may be mentioned more especially anionic surfactants used alone or mixed, such as alkali metal salts, magnesium salts, ammonium salts, amine salts or alkanolamine salts of the following compounds:

alkyl sulphates, alkyl ether sulphates, ethoxylated or non-ethoxylated alkylamide sulphates, alkylsulphonates, alkylamidosulphonates, alpha-olefinsulphonates;

alkyl sulphoacetates;

the alkyl radicals of these compounds having a linear chain of 12 to 18 carbon atoms.

It is also possible to use, in the form of salts mentioned above, fatty acids such as lauric, myristic, oleic, ricinoleic, palmitic or stearic acids, coconut oil acid or hydrogenated coconut oil acid, or carboxylic acids of polyglycol ethers.

By way of cationic surfactants, there may be mentioned more especially fatty amine salts, quaternary ammonium salts such as alkyldimethylbenzylammonium, alkyltrimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long-chain groups preferably having 12 to 18 carbon atoms. Amine oxides may also be mentioned among these compounds of a cationic nature.

Among amphoteric surfactants which can be used, there may be mentioned, in particular, alkylaminomono- and -dipropionates, betaines, such as alkylbetaines, N-alkylsulphobetaines and N-alkylaminobetaines, the alkyl radical having 1 to 22 carbon atoms, and cycloimidinium compounds such as alkylimidazolines.

Among nonionic surfactants which can optionally be used in the compositions according to the invention, there may be mentioned condensation products of a monoalcohol, alpha-diol, alkylphenol or amide with glycidol, such as the compounds described in French Pat. Nos. 2,091,516, 2,169,787 and 2,328,763; the compounds of formula:

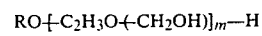

$$RO{+}C_2H_3O{+}CH_2OH)]_m{-}H$$

in which R denotes an alkyl, alkenyl or alkylaryl radical having 8 to 22 carbon atoms, and $1 \leq m \leq 10$; polyethoxylated or polyglycerolated alcohols, alkylphenols or fatty acids having a $C_8$ to $C_{18}$ linear fatty chain; condensates of ethylene oxide and propylene oxide with fatty alcohols; polyethoxylated fatty amides containing at least 5 moles of ethylene oxide; and polyethoxylated fatty amines.

The thickening products which can be added to the composition according to the invention are advantageously selected from sodium alginate, gum arabic, guar gum, cellulose derivatives such as methylcellulose, hydroxyethylcellulose, hydropropylmethylcellulose, sodium salt of carboxymethylcellulose and acrylic acid polymers; inorganic thickening agents such as bentonite can also be used. These thickeners are used alone or mixed, and are preferably present in a proportion from 0.5 to 5% by weight relative to the total weight of the composition, and advantageously from 0.5 to 3% by weight.

The dyeing compositions according to the invention can be formulated at acid, neutral or alkaline pH, and the pH can vary from, say, 4 to 10.5, and preferably from 6 to 10. Among the alkalization agents which can be used, there may be mentioned alkanolamines and alkali metal or ammonium hydroxides and carbonates. Among acidification agents which can be used, there may be mentioned lactic acid, acetic acid, tartaric acid, phosphoric acid, hydrochloric acid and citric acid.

The dyeing compositions according to the invention can contain, in addition, various conventional adjuvants such as antioxidants, perfumes, sequestering agents, film-forming products and treatment agents, dispersants, hair conditioning agents, preservatives and opacifiers, as well as any other adjuvants customarily used in cosmetics.

The dyeing composition according to the invention can take various conventional forms for hair dyeing, such as thickened or gelified liquids, creams or aerosol foams, or any other forms suitable for carrying out dyeing of keratinous fibres.

When it contains at least one oxidation base, the dyeing composition according to the invention is mixed, at the time of use, with oxidizing agents such as peroxides and alkali metal persalts such as hydrogen peroxide, sodium peroxide, potassium peroxide, sodium perborate, sodium percarbonate and urea peroxide.

The present invention also provides a process for dyeing keratinous fibres, and especially human hair, characterized in that the dyeing composition defined above is allowed to act on the dry or damp keratinous fibres. The compositions according to the invention can be used as non-rinsed lotions when the compositions do not contain an oxidation dye, that is to say the compositions according to the invention are applied to the keratinous fibres and these are then dried without intermediate rinsing. In other modes of use, the dyeing compositions according to the invention are applied to the keratinous fibres for, say, 3 to 60 minutes, preferably 5 to 45 minutes, and the fibres are then rinsed, optionally washed and rinsed again, and then dried.

The dyeing compositions according to the invention can be applied on natural or dyed hair which has been permanently waved or otherwise, or to strongly or to lightly bleached hair, optionally permanently waved.

The following Examples further illustrate the present invention.

EXAMPLE A

Preparation of 4-[(β-hydroxyethyl)(γ-hydroxypropyl)amino]-2-nitro-1-[(β-hydroxyethyl)amino]benzene mononhydrochloride To a suspension of 0.15 mole (15 g) of potassium carbonate in 60 ml of water to which 0.30 mole (28.4 g) of 3-chloro-1-propanol has been added, 0.1 mole (241 g) of 4-(β-hydroxyethyl)amino-2-nitro-N-(β-hydroxyethyl)aniline is added.

The mixture is heated on a boiling waterbath for 10 hours. After the reaction medium has been filtered hot in order to remove inorganic salts, the cooled filtrate is extracted with ethyl acetate. After drying, and evaporation of the ethyl acetate, 35.5 g of a violet oil are obtained.

This oil is taken up in 150 ml of absolute alcohol; 35 ml of a 7N solution of hydrochloride acid in ethanol are added; the hydrochloride formed crystallizes from the medium.

After the crystals are drained, washed with absolute ethanol and recrystallized from ethanol, 0.054 mole (18 g) of the expected product is obtained.

Molecular mass calculated for $C_{13}H_{22}ClN_3O_5$: 335.8
Molecular mass found by potentiometric assay in water by sodium hydroxide: 343

The analysis of the product obtained gives the following results:

| Analysis | Calculated for $C_{13}H_{22}ClN_3O_5$ | Found |
|---|---|---|
| C% | 46.50 | 46.62 |
| H% | 6.60 | 6.70 |
| N% | 12.51 | 12.47 |
| O% | 23.82 | 23.89 |
| Cl% | 10.56 | 10.50 |

EXAMPLE B

Preparation of 4-bis(β-hydroxyethyl)amino-2-nitro-1-[(γ-hydroxypropyl)amino]benzene monohydrochloride In 60 ml of 3-amino-1-propanol, 0.07 mole (17.1 g) of 4-fluoro-3-nitro-N,N-bis(β-hydroxyethyl)aniline (described in Example 2 of French Pat. No. 1,581,135) are dissolved with stirring. After being heated for three quarters of an hour on a boiling waterbath, the reaction medium is poured onto 300 g of ice. Most of the 3-amino-1-propanol is neutralized by adding 35 ml of concentrated hydrochloric acid.

After extraction with ethyl acetate, drying, and evaporation of the ethyl acetate under vacuum, a violet oil is obtained which is dissolved in 100 ml of absolute ethanol. The addition of 25 ml of a solution of hydrochloric acid in absolute ethanol enables the hydrochloride of the expected product to be precipitated.

The hydrochloride is drained and washed with isopropanol. After recrystallization from 110 ml of absolute ethanol, 0.52 mole (17.4 g) of the expected product is obtained.

Molecular mass calculated for $C_{13}H_{22}N_3O_5Cl$: 335.8
Molecular mass found by potentiometric assay in water by sodium hydroxide: 333.5

The analysis of the product obtained gives the following results:

| Analysis | Calculated for $C_{13}H_{22}N_3O_5Cl$ | Found |
|---|---|---|
| C% | 46.5 | 46.48 |
| H% | 6.6 | 6.59 |
| N% | 12.51 | 12.38 |
| O% | 23.82 | 24.00 |
| Cl% | 10.56 | 10.40 |

EXAMPLE C

Preparation of 4-bis(β-hydroxyethyl)amino-2-nitro-1-[(β-hydroxypropyl)amino]benzene hydrochloride First stage: Preparation of 4-fluoro-3-nitro-1-[bis(β-hydroxethyl)amino]benzene This preparation is described in French Pat. No. 1,581,135.

Second stage: Preparation of 4-bis(β-hydroxyethyl)amino-2-nitro-1-[(β-hydroxypropyl)amino]benzene hydrochloride.

In 70 ml of 1-amino-2-propanol, 0.07 mole (17.1 g) of 4-fluoro-3-nitro-1-[bis(β-hydroxyethyl)amino]benzene is dissolved with stirring. After being heated for three quarters of an hour on a boiling waterbath, the reaction medium is poured onto 300 g of ice.

After addition of 55 ml of concentrated hydrochloric acid, the mixture is extracted with ethyl acetate. After drying, and evaporation of the ethyl acetate, 22.6 g of the expected product are obtained, and this is converted to hydrochloride by dissolution in 100 ml of absolute ethanol to which 50 ml of hydrochloric acid solution in absolute ethanol are added.

The hydrochloride thereby formed is drained and washed with isopropanol. After recrystallization from 95° strength ethanol and drying, 18.6 g of the expected product are obtained.

Molecular mass calculated for $C_{13}H_{22}N_3O_5Cl$: 335.80
Molecular mass found by potentiometric assay in water by sodium hydroxide: 334

The analysis of the product obtained gives the following results:

| Analysis | Calculated for $C_{13}H_{22}N_3O_5Cl$ | Found |
|---|---|---|
| C% | 46.50 | 46.31 |
| H% | 6.60 | 6.61 |
| N% | 12.51 | 12.55 |

-continued

| Analysis | Calculated for $C_{13}H_{22}N_3O_5Cl$ | Found |
|---|---|---|
| O% | 23.82 | 23.80 |
| Cl% | 10.56 | 10.48 |

EXAMPLE 1

The following composition is prepared:

| | |
|---|---|
| Methylamino-1-nitro-4-[bis($\beta$-hydroxyethyl)-amino]benzene | 1.40 g |
| 1-($\alpha$-Hydroxypropyl)amino-2-nitro-4-[bis($\beta$-hydroxyethyl)amino]benzene monohydrochloride | 2.10 g |
| 1-Nitro-2-amino-3-hydroxybenzene | 0.40 g |
| 3-Methylamino-4-nitrophenyl $\beta,\alpha$-dihydroxypropyl ether | 0.60 g |
| 1-($\beta$-Hydroxyethyl)amino-2-nitro-4-aminobenzene | 0.45 g |
| 1-($\beta$-Hydroxyethyl)amino-2-nitro-4-hydroxybenzene | 0.30 g |
| [4-($\beta$-hydroxyethyl)amino-3-nitrophenoxy]-ethanol | 0.3 g |
| Lauric diethanolamide | 3 g |
| Lauric acid | 1.5 g |
| Nonylphenol treated with 9 moles of ethylene oxide | 3.5 g |
| 2-Butoxyethanol | 5 g |
| Hydroxyethylcellulose sold by HERCULES under the name "Natrosol 250 HHR" | 0.15 g |
| 2-Amino-2-methyl-1-propanol q.s. | pH 9.5 |
| Demineralized water q.s. | 100 g |

This composition is applied for 30 min to dark chestnut-colored hair. The composition is rinsed. The hair is then tinted a dark auburn-brown shade.

EXAMPLE 2

The following composition is prepared:

| | |
|---|---|
| 1-($\beta$-Hydroxyethyl)amino-2-nitro-4-[bis($\beta$-hydroxyethyl)amino]benzene | 1.5 g |
| 1-Methylamino-2-nitro-4-[bis($\beta$-hydroxyethyl)amino]benzene | 1.3 g |
| 1-($\beta$-Hydroxypropyl)amino-2-nitro-4-[bis($\beta$-hydroxyethyl)amino]benzene monohydrochloride | 1.3 g |
| 1-($\beta$-Hydroxyethyl)amino-2-nitro-4-[($\beta$-hydroxyethyl)($\alpha$-hydroxypropyl)-amino]benzene monohydrochloride | 1 g |
| 1-Amino-2-nitro-4-[$\beta$-hydroxyethyl)-amino]benzene | 0.6 g |
| 1 1-($\beta$-Hydroxyethyl)amino-2-nitro-4-aminobenzene | 0.6 g |
| 1-Amino-2-nitro-4-($\beta$-hydroxyethyl)amino-5-methylbenzene | 0.05 g |
| Oleic diethanolamide | 5 g |
| Nonylphenol treated with 9 moles of ethylene oxide | 10 g |
| 2-Ethoxyethanol | 10 g |
| 2-Amino-2-methyl-1-propanol q.s. | pH = 9.5 |
| Demineralized water q.s. | 100 g |

This composition is applied on dark chestnut-colored hair. The composition is rinsed after 30 minutes' exposure. Hair having a purple-violet dark brown shade is thereby obtained.

We claim:

1. A hair dye composition for living human hair comprising a solution in water, as a cosmetically acceptable vehicle, of (1) a paraphenylene diamine selected from the group consisting of (a) a 2-nitroparaphenylene diamine of the formula

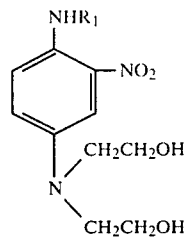

wherein $R_1$ represents alkyl having 1–3 carbon atoms or $\beta$-hydroxyalkyl and (b) an inorganic or organic salt of the 2-nitro paraphenylene diamine defined in (a), said paraphenylene diamine being present in an amount ranging from 0.05 to 10 percent by weight, expressed as free based, based on the total weight of said composition, and (2) a co-solubilizing amount of a compound selected from the group consisting of (c) a compound having the formula

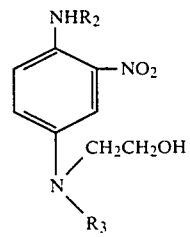

wherein $R_2$ represents hydroxyalkyl wherein the alkyl moiety has 2–3 carbon atoms; and $R_3$ represents $\omega$-hydroxyalkyl wherein the alkyl moiety has 2–3 carbon atoms, with the proviso that when $R_3 = CH_2CH_2OH$, $R_2$ does not represent $\beta$-hydroxyethyl, and (d) an inorganic or organic salt of the compound defined in (c), said compound of (2) being present in an amount ranging from 0.1 to 10 percent by weight, expressed as free base, based on the total weight of said composition.

2. The hair dye composition of claim 1 wherein $R_1$ is methyl or $\beta$-hydroxyethyl.

3. The hair dye composition of claim 1 wherein one of $R_2$ and $R_3$ is $\beta$-hydroxyethyl and the other is $\gamma$-hydroxypropyl.

4. The hair dye composition of claim 3 wherein $R_3$ is $\beta$-hydroxyethyl and $R_2$ is $\beta$-hydroxypropyl.

5. The hair dye composition of claim 1 wherein said paraphenylene diamine is present in an amount ranging from 0.1 to 5 percent by weight, expressed as free base, based on the total weight of said composition.

6. The hair dye composition of claim 1 wherein said compound of (2) is present in an amount ranging from 0.3 to 5 percent by weight, expressed as free base, based on the total weight of said composition.

7. The hair dye composition of claim 1 wherein said cosmetically acceptable vehicle also includes an organic solvent, present in an amount ranging from 0.5 to 20 weight percent based on the total weight of said composition, said organic solvent being selected from the group consisting of ethyl alcohol, isopropyl alcohol, benzyl alcohol, phenylethyl alcohol, ethylene glycol, the monomethyl, monoethyl or monobutyl ether of ethylene glycol, propylene glycol, butylene glycol, dipropylene glycol, diethylene glycol monoethyl ether and diethylene glycol monobutyl ether.

8. The hair dye composition of claim 7 wherein said cosmetically acceptable vehicle is present in an amount ranging from 2 to 10 percent based on the total weight of said composition.

9. The hair dye composition of claim 1 which also includes a mono- or diethanolamide of an acid derived from copra, lauric acid or oleic acid, present in an amount ranging from 0.05 to 10 weight percent based on the total weight of said composition.

10. The hair dye composition of claim 1 which also contains a surfactant present in an amount ranging from 0.1 to 50 weight percent based on the total weight of said composition.

11. The hair dye composition of claim 1 which also contains a thickening agent present in an amount ranging from 0.5 to 5 weight percent based on the total weight of said composition.

12. The hair dye composition of claim 1 having a pH ranging from 4 to 10.5.

13. The hair dye composition of claim 1 having a pH ranging from 6 to 10.

14. A process for dyeing living human hair comprising applying to the hair a hair dyeing amount of the hair dye composition of claim 1, permitting said hair dye composition to remain in contact with the hair for a period of time ranging from 3 to 60 minutes, rinsing the hair and drying the hair.

15. The process of claim 14 wherein subsequent to rinsing the hair and prior to drying the hair, the hair is washed and rinsed.

16. A process for dyeing living human hair comprising applying to the hair a hair dyeing amount of the hair dye composition of claim 1, permitting said hair dye to remain in contact with the hair for a period of time ranging from 3 to 60 minutes and drying the hair without an intermediate rinse thereof.

* * * * *